United States Patent [19]

Kathawala

[11] 4,024,182

[45] May 17, 1977

[54] PREPARATION OF ARYL-BUTADIENOIC ACIDS

[75] Inventor: Faizulla G. Kathawala, West Orange, N.J.

[73] Assignee: Sandoz, Inc., E. Hanover, N.J.

[22] Filed: Aug. 15, 1975

[21] Appl. No.: 605,153

[52] U.S. Cl. .......................... 260/521 R; 260/469; 260/470; 260/473 R; 260/473 F; 260/476 R; 260/515 R; 260/515 A; 260/516; 260/520 R; 260/520 D; 260/521 H; 260/330.5
[51] Int. Cl.² ........................................ C07C 51/00
[58] Field of Search ....... 260/520 R, 521 R, 515 A, 260/515 M, 516, 330.5, 515 R, 520 D, 521 H

[56] References Cited

UNITED STATES PATENTS

| 3,402,198 | 9/1968 | Bolhofer | 260/521 R |
|---|---|---|---|
| 3,445,503 | 5/1969 | Schultz et al. | 260/521 R |
| 3,452,081 | 6/1969 | Sprague et al. | 260/520 R |
| 3,674,836 | 7/1972 | Creger | 260/521 R |

OTHER PUBLICATIONS

Moppett et al., "J. Chem. Soc.," 1968(c), pp. 3040–3042.
Rosenfeld, "J. Am. Chem. Soc.," vol. 79, pp. 5540–5542, (1957).
Fieser et al., "Reagents for Org. Synthesis," John Wiley and Sons, New York, pp. 1276–1279, 1292–1293, (1966).
Woodward et al., JACS, 88; 582–583, (1966).
Pike et al., "J. Org. Chem.," 34, 3552–3557, (1969).
Eckstein, "Angew. Chem.," 77, 912–913, (1965) and 78, 682–683, (1966).

*Primary Examiner*—Norman Morgenstern
*Attorney, Agent, or Firm*—Gerald D. Sharkin; Richard E. Vila; Frederick H. Weinfeldt

[57] ABSTRACT

Aryl-butadienoic acids, e.g., 4-(p-tetradecyloxyphenyl)-2-methyl-buta-2,3-dienoic acid, are prepared by a process comprising converting an acyl halide of an aryl lower alkanoic acid to its corresponding $\beta,\beta,\beta$-trichloroethyl ester of the desired aryl-butadienoic acid which is then treated with zinc to obtain the corresponding free arylbutadienoic acid.

9 Claims, No Drawings

PREPARATION OF ARYL-BUTADIENOIC ACIDS

This invention relates to a chemical process, and more particularly to a process for the preparation of arylbutadienoic acids and intermediates therein.

The aryl-butadienoic acid compounds involved in this invention may be conveniently represented by the formula I:

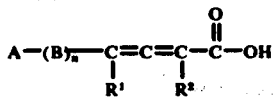

wherin n is 0 or 1;
each of $R^1$ and $R^2$, independently, is a hydrogen atom or alkyl having from 1 to 4 carbon atoms;
B is

wherein each of $R^4$ and $R^5$ is alkyl having from 1 to 3 carbon atoms, which may be like or unlike, preferably methyl;
A is

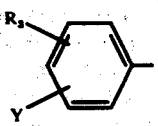

wherein
Y is a hydrogen atom, alkyl having from 1 to 4 carbon atoms, alkoxy having from 1 to 24 carbon atoms, alkylthio having from 1 to 24 carbon atoms, halo having an atomic weight of from about 19 to 36, i.e., fluoro or chloro, cyclohexyl, phenoxy or substituted or unsubstituted phenyl of the formula

wherein
X is a hydrogen atom, halo having an atomic weight of from about 19 to 36, i.e., fluoro or chloro, alkoxy having from 1 to 4 carbon atoms or alkyl having from 1 to 4 carbon atoms, preferably a hydrogen atom;
n' is an integer from 1 to 2, preferably n' is 1;
$R^3$ is a hydrogen atom, alkyl having from 1 to 3 carbon atoms or halo having an atomic weight of from about 19 to 36, i.e., fluoro or chloro; or when n is 0
A is

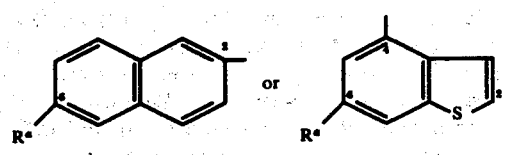

wherein
$R^a$ is hydrogen, halogen having an atomic weight of from about 19 to 36, i.e., fluoro or chloro, alkyl having from 1 to 4 carbon atoms, alkoxy having from 1 to 4 carbon atoms, preferably methoxy, alkylthio having from 1 to 4 carbon atoms, or difluoromethoxy.

With reference to the definitions of alkyl, alkoxy and alkylthio above, it is intended that when any of them have from 1 to 3 carbon atoms, the alkyl portion thereof may be methyl, ethyl, n-propyl or isopropyl, and when any of them have from 1 to 4 carbon atoms, the alkyl portion thereof includes the above enumerated alkyl groups, as well as the unbranched and branched forms of butyl. Where Y is alkoxy or alkylthio of from 1 to 24 carbon atoms, two classes are contemplated, i.e., the class having from 1 to 4 carbon atoms, (a lower alkyl moiety) and those having from 5 to 24 carbon atoms (i.e., a higher alkyl moiety) such as pentyl, hexyl, octyl, decyl, dodecyl, tetradecyl, hexadecyl or octadecyl which may be branched or unbranched, preferably having from 5 to 16 carbon atoms.

The process for the preparation of Compounds I may be conveniently represented in Reaction Scheme D, below, in which the substituents A, B, n, $R^1$ and $R^2$ are as defined above; the particular process steps and compounds involved being described hereinafter. The process is particularly advantageous in preparing Compounds I in which A is a phenyl-type radical in which Y is alkoxy or alkylthio having from 5 to 24 carbon atoms.

REACTION SCHEME D

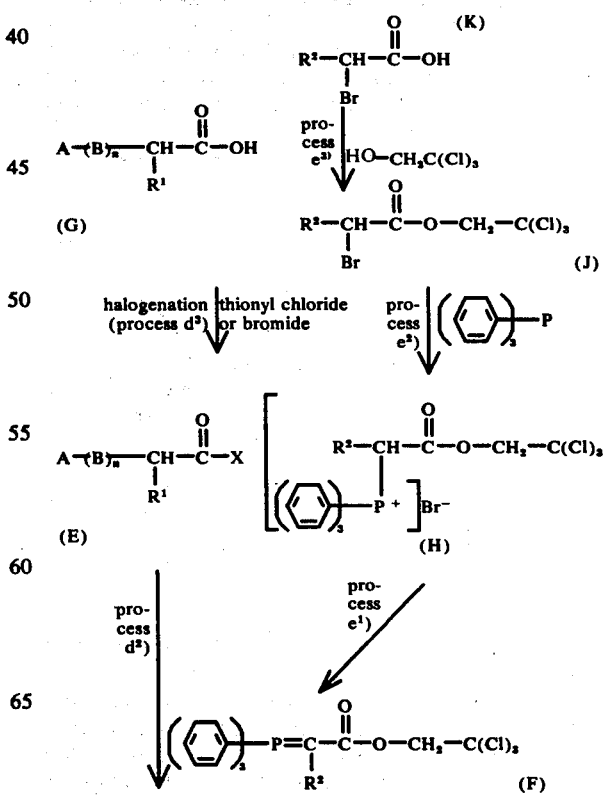

-continued

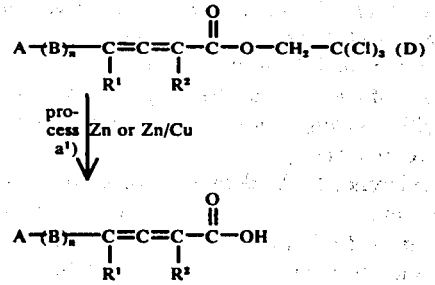

Process d¹ comprises treating a corresponding trichloroethyl ester of the desired Compound I, i.e., a compound D:

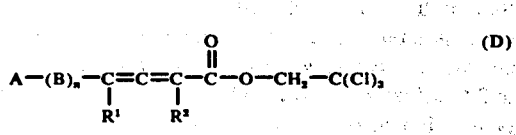

in which A, B, n, R¹ and R² are as defined above, in a suitable reaction medium, in the presence of finely divided zinc or zinc-copper, preferably finely divided zinc-copper, e.g. as dust.

In carrying out process d¹, a suitable reaction medium is one which is inert and serves as a solvent for compounds D, e.g., concentrated aqueous acetic acid when zinc is used and dimethyl formamide when zinc-copper is used. Reaction temperatures are moderate, e.g., those of from about 20° to 35° C. The zinc-copper reagent may be obtained by the procedure described by E. Le Goff in the Journal of Organic Chemistry, 29, 2048 (1964). Essentially anhydrous conditions are employed when zinc-copper is used and are achieved by means conventionally practiced where it is desired to essentially exclude moisture, e.g., by the use of absolute (dry) reaction medium and reagents, employing moisture-free apparatus and excluding moisture-laden air. The concentrated aqueous acetic acid medium has from about 70 to 95% acetic acid, preferably about 90%, (volume/volume).

Compounds D, described above, are obtainable by reaction of an acyl halide of formula E:

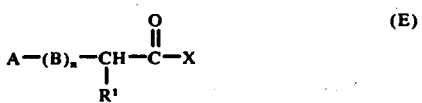

in which A, B, n and R¹ are as defined above, and X is halo having an atomic weight from about 34 to 80, preferably chloro, with a, $\beta,\beta,\beta$-trichloroethyl phosphorous ester of the formula F:

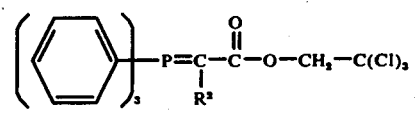

in which R² is as defined above, in a solvent under essentially anhydrous conditions (process d²).

Process d²) may be conveniently carried out in an inert organic solvent, such as cyclic ether, e.g., tetrahydrofuran, and at an elevated temperature, e.g., from about 50° to 100° C, preferably at the reflux temperature of the reaction mixture. Essentially, anhydrous conditions may be achieved in the manner described above with respect to process d¹).

Compounds E are known and may be prepared by methods described in the literature, or where not known may be attained by methods described in the literature for the preparation of known compounds, e.g., by halogenation of corresponding carboxylic acid forms, i.e., compounds of formula G (process d³):

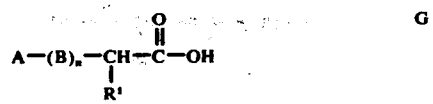

in which A, B, n and R¹ are as defined above.

Process d³) may be carried out in the conventional manner for the conversion of a carboxylic acid to its acyl halide, e.g., by treatment with thionyl chloride or thionyl bromide (depending upon whether it is desired that X be chloro or bromo) at elevated temperatures, e.g., from about 50 to 160° C, preferably at the reflux temperature of the reaction mixture under essentially anhydrous conditions. An inert solvent such as an aromatic solvent, e.g., benzene, toluene or xylene, may be used, or the halogenating agent may be employed in large excess to serve as solvent.

The trichloroethyl ester reactants (Compounds F) used in process d¹), above, are obtainable by a series of reaction steps starting with the reaction of $\beta,\beta,\beta$-trichloroethanol with an $\alpha$-R², $\alpha$-bromo-substituted acetic acid (i.e., a compound of formula K), (process e³), to obtain a corresponding trichloroethanol ester of the particular $\alpha$-bromo alkanoic acid, i.e., a compound J; which is then reacted (process e²) with triphenylphosphine to obtain a phosphoryl bromide compound (compound H) which is then reacted (process e¹) with an aqueous solution of an alkali metal hydroxide to obtain the desired compound F, as is shown in Reaction Scheme D, above.

The above-described esterification, (process e³), is carried out in the conventional manner, e.g. under strongly acidic conditions, which may be provided by the inclusion of a mineral acid, preferably concentrated sulfuric acid, in the presence of an inert solvent, particularly one which forms an azeotrope with water, e.g., an aromatic solvent, such as benzene, toluene or xylene, preferably toluene, at temperatures of e.g., from about 80° to 160° C. preferably at the reflux temperature of the reaction mixture, under conditions in which water formed in the reaction zone, preferably by employing a Dean-Stark trap.

Process e²), the condensation of a resulting $\alpha$-bromo acetic acid ester with triphenylphosphine may be carried out in the presence of an inert solvent, e.g., an aromatic solvent such as benzene, toluene or xylene, preferably benzene, at a temperature of from about 60° to 140° C., e.g. at the reflux temperature of the reaction mixture, under essentially anhydrous conditions.

Process e¹) is carried out under dehydrohalogenating conditions by treating the desired phosphoryl compound (a compound H) with an aqueous solution of an alkali metal hydroxide, such as sodium hydroxide or potassium hydroxide, preferably sodium hydroxide (at e.g. about 5 to 15% w/v concentration), preferably in the presence of an inert solvent such as methylene chloride, at moderate temperatures, e.g., from about 15° to 50° C., e.g. at room temperature.

Other above-described starting materials and reagents, e.g., Compounds G and K are known, and are obtainable by methods described in the literature; some being commercially available, or where not known, may be prepared by methods analogous to those described in the literature for the preparation of those compounds which are known.

The above-described final compounds and intermediates may be recovered and refined by conventional techniques, e.g., by crystallization, distillation or chromatographic techniques, e.g., thin-layer or column chromatography, as is appropriate.

The compounds of formula I are useful because they possess pharmacological activity in animals. In particular, the Compounds I are useful as anti-inflammatory agents and as hypolipidemic agents.

The activity of Compounds I as anti-inflammatory agents is indicated by the Carrageenan induced edema test on rats (oral administration at 10 to 200 mg/kg). For such use, the compounds may be combined with a pharmaceutically acceptable carrier, and such other conventional adjuvants as may be necessary, and administered orally in such forms as tablets and capsules, elixirs, suspensions and the like or parenterally in the form of an injectable solution or suspension. The dosage administered will, of course, vary depending upon the compounds used and mode of administration. However, in general, satisfactory results are obtained when administered at a daily dosage of from about 1 mg to about 250 mg per kilogram, e.g., from about 1 mg to about 175 mg per kg of body weight, preferably given in divided doses 2 to 4 times a day, or in sustained release form. For most mammals, the administration of fromm about 100 mg to about 3000 mg, e.g., from about 160 mg to about 2000 mg, of the compound per day provides satisfactory results and dosage forms suitable for internal administration comprise from about 25 mg to about 1500 mg, e.g., from about 40 mg to about 1000 mg, of the compound in admixture with a solid or liquid pharmaceutical carrier or diluent.

The activity of compounds I as hypolipidemic agents, particularly hypolipoproteinemia agents, is evidenced, for example, by lowering cholesterol and triglyceride blood serum levels in tests on a group of white rats which are given typically 10 to 50 milligrams per kilogram of body weight per diem of the compound orally, for 6 days, followed by extraction with isopropanol of serum or plasma after anesthetizing the rats with sodium hexobarbital, and then noting the cholesterol and triglyceride contents as compared to those of a control group. The cholesterol and triglyceride are determined by the methods described by Lofland, H. B., Anal. Biochem. 9:393 (1964) : (Technicon method N 24a) : and G. Kessler and H. Lederer, Technicon Symposium, Mediad Inc., New York, pages 345–347 (1956), respectively. For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 1 milligram to about 250 milligrams per kilogram of animal body weight, preferably given orally and in divided doses, 2 to 4 times a day, or in sustained release form.

For most mammals the total daily dosage is from about 50 milligrams to about 2000 milligrams of the compound, and dosage forms suitable for internal administration comprise from about 12.5 to 1000 milligrams of the compound in admixture with a solid or liquid pharmaceutically acceptable carrier or diluent.

For above uses, compounds I may be administered orally in such forms as tablets, dispersible powders, granules, capsules, syrups and elixirs; and parenterally as solutions, suspensions, dispersions, emulsions, and the like, e.g. a sterile injectable solution such as an aqueous suspension. These pharmaceutical compositions may contain from about 0.5% up to about 90% of the active ingredient in combination with the carrier or adjuvant, more usually between 4% and 60% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g. inert diluents such as calcium phosphate, calcium sulphate dihydrate, lactose and talc, granulating and disintegrating agents, e.g. starch and alginic acid, binding agents, e.g. starch, gelatin, polyvinyl pyrrolidone and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g. calcium carbonate, calcium phosphate, kaolin, polyoxyethylene glycol, peanut oil, sesame oil and corn oil.

Convenient unit dosage forms for the above-described users are those having from about 12.5 to 1500 mg., preferably about 12.5 to 500 mg. of a compound I as active ingredient. The preferred pharmaceutical compositions from the standpoint of preparation and ease of administration are solid orally administrable compositions, particularly tablets and solid or liquid diluent-filled capsules (as appropriate to the nature of the particular active ingredient), containing, e.g. from about 12.5 to 500 mg. of the active ingredient.

It will be appreciated that compounds I are carboxylic acids which can form salts. The pharmaceutically acceptable salts thereof are included within the scope of the pharamaceutically useful compounds of the present invention. Such salts are the pharmaceutical equivalents of their acid forms, and include, by way of illustration, the sodium salt and the triethyl ammonium salt. In general, the salts may be produced from the free acids by established procedures. Conversely, the free acids may be obtained from the salts by well-known procedures. It will be appreciated that while the Compounds I are generally referred to in the processes herein described as "acid forms," they may actually be present in the form of their corresponding salts under particular reaction conditions, and may be recovered directly in pharmaceutically acceptable salt form, by conventional methods.

Capsules and tablets containing the ingredients indicated below may be prepared by conventional techniques and are useful in treating inflammation or lipidemia, particularly hyperlipoproteinemia, in mammals at a dose of one capsule or tablet two to four times per day;

| Ingredient | Weight in Milligrams | | |
|---|---|---|---|
| | Tablet | Capsule | Capsule |
| 4-(p-tetradecyloxyphenyl)-2-methyl-buta-2,3-dienoic acid | 50 | 50 | 30 |
| Tragacanth | 10 | | |
| Lactose | 197.5 | 170 | |
| Corn Starch | 25 | | |
| Talcum | 15 | | |
| Magnesium Stearate | 2.5 | | |
| Polyethylene Glycol (M.W. 6000) | | | 300 |

In the following examples, which are illustrative of the invention, temperatures are in degrees centigrade, and room temperature is 20° to 30° C., unless indicated otherwise.

EXAMPLE 4-(p-Tetradecyloxyphenyl)-2-methyl-buta-2,3-dienoic acid

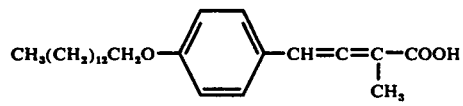

Step A

Preparation of
β,β,β-Trichloroethyl-2-bromopropionate

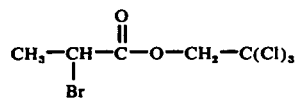

To a solution of 500 g. 2-bromopropionic acid and 488.5 g. 2,2,2-trichloroethanol in 1000 ml. dry toluene is added 1.5 ml. concentrated sulphuric acid. The reaction mixture is then refluxed with a Dean-Stark trap for 4 hours. After cooling, the organic phase is washed three times with 10% aqueous sodium bicarbonate (weight/volume) solution, then with distilled water, dried over anhydrous sodium sulfate, filtered and solvent removed i.v. to give crude bromo-propionate ester, which is used as such in Step B, below.

STEP B

Preparation of
β,β,β-trichloroethyl-2-(triphenylphosphoryl)-propionate bromide.

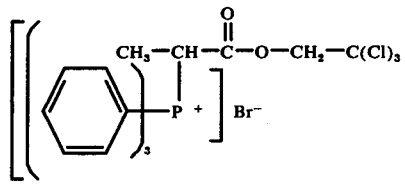

A mixture of 469 g. β,β,β-trichloroethyl-2-bromopropionate and 432.5 g. triphenylphosphine in 1200 ml. dry benzene is refluxed for 16 hours and then cooled. The resultant crystalline title phosphoryl product is filtered off and washed with petroleum ether and dried to give the title phosphoryl product (m.p. 195°–200°).

STEP C

Preparation of
β,β,β-trichloroethyl-2-(triphenylphosphoranylidene)-propionate.

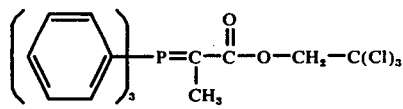

To a solution of 259.5 g. β,β,β-trichloroethyl-2-(triphenylphosphoryl)-propioniate bromide in 2000 ml. methylene chloride is slowly added with vigorous stirring a solution of 22 g. sodium hydroxide in 200 ml. water until the pH of the aqueous layer is brought to 7.5. The reaction mixture is then stirred vigorously for a few more minutes. The organic phase is then washed well with water, dried over anhydrous sodium sulfate, filtered and solvent removed i.v. From the resulting residue is crystallized from ethyl acetate/petroleum ether (10:1), the title triphosphoranylidene product (m.p. 155°–160°).

Step D p-Tetradecyloxyphenylacetylchloride

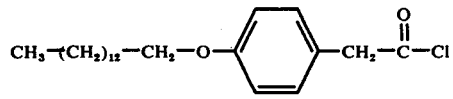

A solution of 10.0 g. p-tetradecyloxyphenylacetic acid in 100 ml. absolute benzene is treated with 19.9 g thionylchloride and refluxed for 2.5 hours. The reaction mixture is then evaporated under vacuum (i.v.) and azeotroped several times with benzene to remove residual thionylchloride, to obtain crude p-tetradecyloxyphenylacetylchloride, which may be used in Step E, below, without further refining.

Step E:

β,β,β-Trichloroethyl-4-(p-tetradecyloxyphenyl)-2-methyl-buta-2,3-dienoate

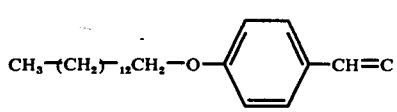
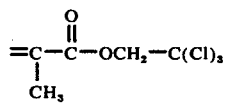

To a solution of 29.3 g. β,β,β-trichloroethyl-2-(triphenylphosphoranylidene)-propionate in 150 ml. absolute tetrahydrofurane (THF) is added 10.0 g. of p-tetradecyloxyphenyl-acetylchloride (obtained by Step A, above, in 50 ml. of absolute tetrahydrofurane. The reaction mixture is refluxed for 45 minutes, cooled in an ice bath, filtered and the filtrate evaporated, i.v. The residue is titurated with petroether, the undesired solids thus obtained are filtered off and the filtrate is once again evaporated i.v. The residue is dissolved in methylene chloride and filtered rapidly through silica gel to obtain crude β,β,β-trichlorethyl-4-(p-tetradecyloxyphenyl)-2-methyl-buta-2,3-dienoate, which may be used as such in Step F, below.

Step F 4-(p-tetradecyloxyphenyl)-2-methyl-buta-2,3-dienoic acid.

To a solution of 5.7 g. β,β,β-trichloroethyl-4-(p-tetracecyloxyphenyl)-2-methyl-2,3-butadienoate in 200 ml. absolute dimethylformamide (DMF) is added 24 g. of ether-wet-zinc-copper dust (prepared according to the procedure of E. LeGoff: J.O.C. 29, 2048 (1964), immediately after filtering; about 50% of the dust weight being residual ether. The reaction mixture is stirred at room temperature for 4 hours, filtered, diluted with 1 liter of ether and the organic phase washed extensively with 2N HCl, then with water, dried over anhydrous sodium sulfate, filtered, and the solvent removed i.v. From the residue is crystallized from pentane the title product, m.p. 85°–90° C.

Repeating the procedure of this Example but replacing the p-tetradecyloxyphenylacetic acid used in Step D, thereof, with an approximately equivalent amount of:
 a. p-decyloxyphenylacetic acid;
 b. p-octadecyloxyphenylacetic acid, or
 c. p-hexadecyloxyphenylacetic acid; there is accordingly obtained:
 a. 4-(p-decyloxyphenyl)-2-methyl-buta-2,3-dienoic acid, m.p. 67°–75°, from pentane;
 b. 4-(p-octadecyloxyphenyl)-2-methyl-buta-2,3-dienoic acid, m.p. 80°–85°, from pentane;
 c. 4-(p-hexadecyloxyphenyl)-2-methyl-buta-2,3-dienoic acid, m.p. 80°–85°, from ether/pentane (10/1).

What is claimed is:
1. A process for the preparation of a compound of the formula

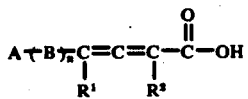

wherein
 n is 0 or 1;
 A is

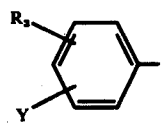

wherein Y
 is a hydrogen atom, alkyl having from 1 to 4 carbon atoms, alkoxy having from 1 to 24 carbon atoms, alkylthio having from 1 to 24 carbon atoms, halo having an atomic weight of from about 19 to 36, cyclohexyl, phenoxy or substituted or unsubstituted phenyl of the formula

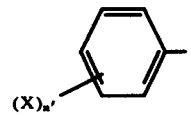

wherein
 X is a hydrogen atom, halo having an atomic weight of from about 19 to 36, alkoxy having from 1 to 4 carbon atoms or alkyl having from 1 to 4 carbon atoms;
 n' is an integer from 1 to 2; and
 $R^3$ is a hydrogen atom, alkyl having from 1 to 3 carbon atoms or halo having an atomic weight of from about 19 to 36; or when n is 0 A is

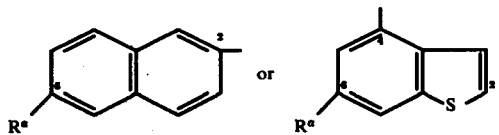

wherein
 $R^a$ is a hydrogen atom, halogen having an atomic weight of from about 19 to 36, alkyl having from 1 to 4 carbon atoms, alkoxy having from 1 to 4 carbon atoms, alkylthio having from 1 to 4 carbon atoms, or difluoromethoxy;
 B is

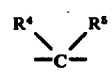

wherein each of $R^4$ and $R^5$ is alkyl having from 1 to 3 carbon atoms which may be like or unlike; and
 each of $R^1$ and $R^2$, independently, is a hydrogen atom or alkyl having from 1 to 4 carbon atoms;
 comprising reacting a corresponding compound of the formula

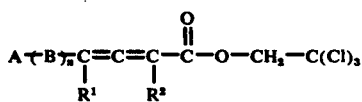

in which A, B, n, $R^1$ and $R^2$ are as defined above, at a temperature of from about 20° to 35° C., in the presence of zinc-copper in finely divided form in dimethylformamide, under essentially anhydrous conditions.
2. A process in claim 1 in which the finely divided zinc - copper is a dust.
3. A process of claim 1 in which $R^2$ is a hydrogen atom.
4. A process of claim 3 in which $R^2$ is methyl.
5. A process of claim 3 in which Y is para-alkoxy.
6. A process of claim 5 in which Y is para-alkoxy having from 5 to 24 carbon atoms.
7. A process of claim 6 in which Y is para-alkoxy having from 5 to 16 carbon atoms.
8. A process of claim 7 in which Y is paratetradecyloxy.
9. A process of claim 1 in which the compound prepared is 4-(p-tetradecyloxyphenyl)-2-methyl-buta-2,3-dienoic acid.

* * * * *